US008894861B2

(12) United States Patent
Podella et al.

(10) Patent No.: US 8,894,861 B2
(45) Date of Patent: Nov. 25, 2014

(54) METHOD OF HERDING AND COLLECTION OF OIL SPILLED AT THE AQUATIC SURFACE

(75) Inventors: Carl W. Podella, Irvine, CA (US); John W. Baldridge, Newport Beach, CA (US); Michael G. Goldfeld, Irvine, CA (US)

(73) Assignee: Advanced Biocatalytics Corporation, Irvine, CA (US)

( * ) Notice: Subject to any disclaimer, the term of this patent is extended or adjusted under 35 U.S.C. 154(b) by 364 days.

(21) Appl. No.: 13/245,719

(22) Filed: Sep. 26, 2011

(65) Prior Publication Data

US 2012/0074067 A1 Mar. 29, 2012

Related U.S. Application Data

(60) Provisional application No. 61/403,994, filed on Sep. 25, 2010.

(51) Int. Cl.
| | | |
|---|---|---|
| *C02F 1/28* | (2006.01) | |
| *C02F 1/40* | (2006.01) | |
| *C09K 3/32* | (2006.01) | |
| *C07K 14/39* | (2006.01) | |
| *E02B 15/04* | (2006.01) | |
| *C02F 1/68* | (2006.01) | |
| *B01J 20/22* | (2006.01) | |
| *C02F 103/00* | (2006.01) | |
| *C02F 3/34* | (2006.01) | |
| *C02F 101/32* | (2006.01) | |

(52) U.S. Cl.
CPC ............... *E02B 15/041* (2013.01); *C09K 3/32* (2013.01); *C02F 2103/007* (2013.01); *C02F 1/286* (2013.01); *C02F 3/347* (2013.01); *C07K 14/39* (2013.01); *C02F 2305/04* (2013.01); *C02F 1/681* (2013.01); *C02F 2101/32* (2013.01); *B01J 20/22* (2013.01); *C02F 1/682* (2013.01); *C02F 1/285* (2013.01); *Y10S 210/924* (2013.01)
USPC ............ 210/663; 210/691; 210/693; 210/924

(58) Field of Classification Search
CPC ............ C02F 1/40; C02F 1/285; C02F 1/286; C02F 2101/32; C02F 2103/007; C02F 2305/04; E02B 15/04; E02B 15/06; E02B 15/101
USPC .............. 210/242.4, 691, 693, 922, 924, 925, 210/663
See application file for complete search history.

(56) References Cited

U.S. PATENT DOCUMENTS 3,810,835 A * 5/1974 Ferm .............................. 210/749
3,959,134 A * 5/1976 Canevari ........................ 210/749

(Continued)

OTHER PUBLICATIONS

International Search Report and Written Opinion dated Feb. 13, 2012 issued in PCT/US2011/053312.

(Continued)

*Primary Examiner* — Matthew O Savage
(74) *Attorney, Agent, or Firm* — Sam K. Tahmassebi; TechLaw LLP

(57) ABSTRACT

Disclosed are methods of removing oil from an aqueous surface, comprising: surrounding an oil spot on the aqueous surface with an oil-absorbing material; and introducing a solution comprising a surfactant to the oil spot. Also disclosed are the above methods where the oil is not mechanically directed towards the oil-absorbing material, or where the oil-absorbing material is not mechanically directed towards the oil. Also disclosed are the above methods further comprising introducing a solution comprising a protein/surfactant complex to the oil spot, where the protein/surfactant complex comprises a protein component obtained from the fermentation of yeast, comprising a mixture of multiple intracellular proteins, at least a portion of the mixture including yeast polypeptides obtained from fermenting yeast and yeast stress proteins resulting from subjecting a mixture obtained from the yeast fermentation to stress.

17 Claims, 1 Drawing Sheet

(56) References Cited

U.S. PATENT DOCUMENTS

| 3,988,932 | A | | 11/1976 | Baier et al. |
| 4,190,531 | A | | 2/1980 | Falk |
| 4,293,348 | A | * | 10/1981 | Shewmaker ............... 134/22.19 |
| 5,679,247 | A | * | 10/1997 | Burke ........................ 210/242.4 |
| 7,645,730 | B2 | | 1/2010 | Baldridge et al. |
| 7,659,237 | B2 | | 2/2010 | Baldridge et al. |
| 2008/0167445 | A1 | | 7/2008 | Podella et al. |

OTHER PUBLICATIONS

Medrzycka and Lamparska, Π-A isotherms for anionic, cationic and mixed anionic—cationic surfactants. Colloids and Surfaces A: Physicochemical and Engineering Aspects Apr. 30, 2000;164(1):9-18.

* cited by examiner

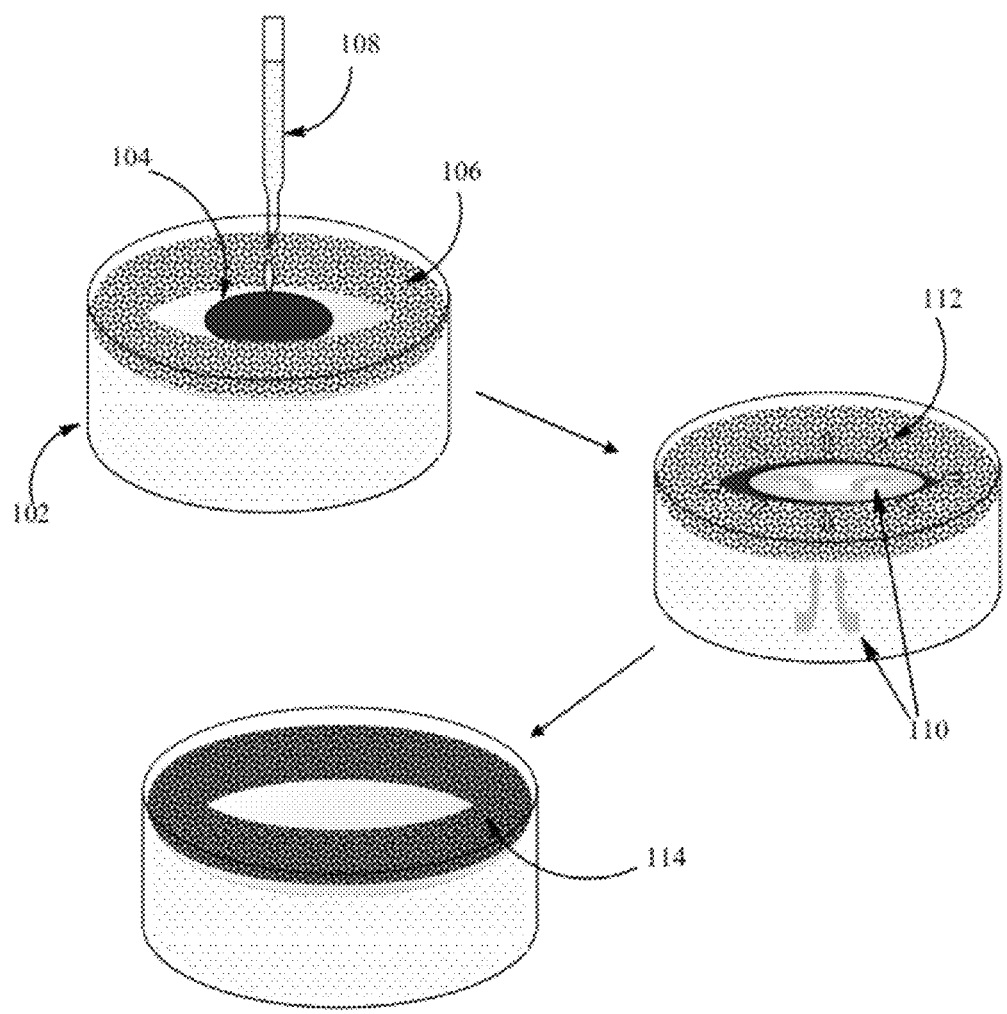

METHOD OF HERDING AND COLLECTION OF OIL SPILLED AT THE AQUATIC SURFACE

RELATED APPLICATIONS

The present application claims priority to the U.S. Provisional Application Ser. No. 61/403,994, filed Sep. 25, 2010, by Goldfeld et al., and entitled "Method Of REMOVAL And Collection Of Oil Spilled At The Aquatic Surface," the entire disclosure of which, including any drawings, is incorporated herein by reference.

FIELD OF THE INVENTION

The invention belongs to the field of methods of cleaning of crude petroleum oil, diesel fuel, and other mostly hydrocarbon (further referred to as "oil") spots from the aquatic surface. The current invention permits the ability to move the oil located on the aquatic surface towards a concentric boom encircling the spill and built out of materials selectively absorbing oil, by the power of surface forces and without applying any mechanical devices for such a directional motion. Oil then is absorbed by the boom and may be either recycled by squeezing out under compression, or utilized as a low-grade fuel.

BACKGROUND OF THE DISCLOSURE

Petroleum oil and its related products, when spilled on a water surface, initially form compact spots of concentric or irregular shapes. The petroleum-based contaminants then spread, are weathered and lose their more volatile components through evaporation and through processing by the hydrocarbonoclastic microorganisms, thus thicken and become more viscous and therefore are more difficult to separate from water.

A widely applied separation technique is based on application of separators—mechanical devices that suck a rather thin surface layer of water with oil, then depose that liquid in their tank for a duration of time necessary to allow the oil to concentrate on the surface of the tank due to the oil buoyancy, then collecting the top layer containing most of the oil for recycling or disposal, while the remaining solution is returned to the water or is also collected and dumped in designated areas.

Another approach consists in collecting oil by a broad variety of oil-absorbing materials that may differ in their selectivity in oil uptake vs. water uptake. In order for such absorption to occur, oil must come into direct contact with the absorbing material. The contact may be achieved e.g. by covering the entire oil spot with such a material, e.g. straw of hay, or some powdered porous hydrophobic inorganic or organic materials, or a compact piece of such a material, e.g. in the form of a boom, or raft, may be mechanically moved across the oil spot, absorbing oil on its way. After the oil uptake, these oil-loaded materials must be collected and are commonly removed and discarded as hazardous waste.

Neither of these approaches provides for an efficient and complete separation of oil from water. In mechanical separators, oil is inevitably collected together with a certain amount of water, and/or the water is not completely freed of oil. In collecting oil by pieces of absorbing material mechanically moved, e.g. by a power boat, it is difficult, if not impossible, to achieve total collection of oil, due to disturbance that such a motion creates on the surface of water, thus interfering with a complete absorption of oil.

SUMMARY OF THE INVENTION

Disclosed are methods of removing oil from an aqueous surface, the method comprising: surrounding an oil spot on the aqueous surface with an oil-absorbing material; and introducing a solution comprising a surfactant to the oil spot. Also disclosed are methods of removing oil from an aqueous surface, the method comprising: surrounding an oil spot on the aqueous surface with an oil-absorbing material; and introducing a solution comprising a surfactant to the oil spot, wherein the oil is not mechanically directed towards the oil-absorbing material, or wherein the oil-absorbing material is not mechanically directed towards the oil. Also disclosed are methods of removing oil from an aqueous surface, the method comprising: surrounding an oil spot on the aqueous surface with an oil-absorbing material; and introducing a solution comprising a protein/surfactant complex to the oil spot, wherein the protein/surfactant complex comprises a protein component obtained from the fermentation of yeast, wherein the protein component comprises a mixture of multiple intracellular proteins, at least a portion of the mixture including yeast polypeptides obtained from fermenting yeast and yeast stress proteins resulting from subjecting a mixture obtained from the yeast fermentation to stress.

BRIEF DESCRIPTION OF THE DRAWINGS

FIG. 1 is a schematic showing the bench-scale demonstration of the oil cleanup methods.

DETAILED DESCRIPTION OF THE EMBODIMENTS

Disclosed herein are method for herding, and collection of oil slicks from the surface of water, together with the chemicals and materials most appropriate for implementation of the method, and calculation procedures for determining the amount of those chemicals and materials needed for the above operations. In one aspect, the methods consist in encircling the spot with a boom formed by an oil-only absorbing material, and injecting a surfactant solution to the center of the spot, the surfactant being selected with a strong affinity to water and lesser affinity to the oil. Without being bound by a particular theory, the inventors submit that when the surfactant solution is applied, surface tension reduction at the center of the spot pulls water from the underneath bulk of water, spreading a clean, oil-free spot in the middle, and pushing oil to the surrounding boom where oil is absorbed. Then the boom, saturated with oil, may be removed from the water and either recycled by squeezing oil from the absorbing material by compression, or used as fuel, e.g. being added to coal combusted in power stations. The calculation methods are provided to determine the amount of surfactant, needed for the operation based on the dimensions of the oil spot, and the amount of absorbing material necessary, based on the oil-absorbing capacity of that boom material.

The methods disclosed herein use a known effect of displacement of floating material by spreading out the area surrounding the point of injection of the surfactant. In one embodiment, such a material is the oil spot, and the methods disclosed herein specify characteristics of surfactant(s) most appropriate for such an effect, since some surfactants would disperse and emulsify oil, rather than push it away from the point of their injection. Although dispersing of major oil spills in the ocean have been widely applied to clean the surface of the water, its shortcoming consist in the fact that dispersing does not actually remove oil from water, and, in fact, makes oil separation more difficult, if not impossible, even though it may speed up the microbiological remediation of oil-contaminated water. The methods disclosed herein also specify the process for application of a surfactant solution to the spots, and provide the calculative procedure to estimate the most appropriate amount of surfactant to be applied based on the dimensions of the oil spill in hand and the surface area encircled by the absorbing boom. Finally, methods disclosed herein specify the types of oil-absorbing materials most appropriate for the entire operation and the ways of the further treatment of these materials through recycling or combustion.

Thus, in one aspect, disclosed herein are methods of removing oil from an aqueous surface, the method comprising surrounding an oil spot on the aqueous surface with an oil-absorbing material, and introducing a solution comprising a surfactant to the oil spot.

In some embodiments, the oil is not mechanically directed towards the oil-absorbing material, or the oil-absorbing material is not mechanically directed towards the oil. Instead, oil is moved (herded) towards the surrounding oil-absorbing boom by tangential force emerging from the drop in surface tension of water by injection of an appropriate surface-active agent to the center of the spot.

In some embodiments, the surfactant solution is injected at the center of the oil spot. In some of these embodiments, the surfactant solution is injected as a strong and narrow flow to the center of the spot. In other embodiments, the surfactant solution is sprayed uniformly at the surface of the oil spot.

In one embodiment, an oil spot on a water surface is surrounded by an oil-absorbing material. The oil-absorbing material can be made from a material selected from the group consisting of sponge, hair, hay, absorbent polymers, and the like. In some embodiments, the oil-absorbing material is contained in a water and oil permeable casing or shell, which allows for contaminated water and oil to come into contact with the oil-absorbing material, but does not allow the oil-absorbing material to escape the casing. Once the oil spot is surrounded, a surfactant solution is injected to the center of the oil spot.

In some embodiments, the surfactant is selected in terms of its hydrophilic/lipophylic balance (HLB) in a way that provides for a rather strong affinity to water, and much weaker affinity to oil, in order to avoid an oil dispersion effect. A number of surfactants known in the art can be used in the methods disclosed herein. In some embodiments, the surfactant is used in the form of a protein/surfactant complex.

Surfactants that are useful in the protein/surfactant complex (PSC) may be either nonionic, anionic, amphoteric or cationic, or a combination of any of the above. Suitable nonionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, phosphate esters, and polymeric surfactants. Suitable amphoteric surfactants include betaine derivatives. Suitable cationic surfactants include amine surfactants. Those skilled in the art will recognize that other and further surfactants are potentially useful in the PSC composition. Some examples of surfactants that may be applicable for use in the soil penetration and root uptake compositions described herein include the following:

Anionic: Sodium linear alkylbenzene sulfonate (LABS); sodium lauryl sulfate; sodium lauryl ether sulfates; sodium dioctyl sulfosuccinates; petroleum sulfonates; linosulfonates; naphthalene sulfonates; branched alkylbenzene sulfonates; linear alkylbenzene sulfonates; fatty acid alkylolamide sulfosuccinate; alcohol sulfates.

Cationic: Stearalkonium chloride; ammonium compounds, such as benzalkonium chloride; quaternary ammonium compounds; amine compounds; ethosulfate compounds.

Non-ionic: Dodecyl dimethylamine oxide; coco diethanolamide alcohol ethoxylates; linear primary alcohol polyethoxylate; alkyl phenol ethoxylates; alcohol ethoxylates; EO/PO polyol block polymers; polyethylene glycol esters; fatty acid alkanolamides.

Amphoteric: Cocoamphocarboxyglycinate; cocamidopropyl betaine; betaine derivatives; imidazoline derivatives.

Several of the known surfactants are non-petroleum based. For example, several surfactants are derived from naturally occurring sources, such as vegetable sources (coconuts, palm, castor beans, etc.). These naturally derived surfactants may offer additional benefits such as biodegradability.

It should be understood that these surfactants and the surfactant classes described above are identified only as preferred materials and that this list is neither exclusive nor limiting of the compositions and methods described herein.

In some embodiments, the protein mixture used in the PSC is obtained from the fermentation of yeast. The methodology for the fermentation of yeast and obtaining stressed (e.g., heat-shock) proteins from the yeast fermentation process is discussed elsewhere. See, for example, U.S. Pat. Nos. 7,659,237, 7,759,301, and 7,645,730, the entire disclosure of which is incorporated herein by reference in its entirety, especially the passages discussing the post-fermentation stress on the fermentation mixture to obtain low molecular weight proteins.

In some embodiments, the low molecular weight protein factor is obtained from yeast fermentation, preferably aerobic, processes which, when coupled with surfactants, reduce the critical micelle concentration of surfactants, surface tension and interfacial tension of surfactant solutions, with reductions in the critical micelle concentration, surface tension, and interfacial tension as compared to the surfactants taken alone, and further reduction of the same parameters observed after exposure to oil. This factor was found in the yeast fermentation-derived polypeptide fractions ranging in molecular weights between about 6,000 and 17,000 daltons by the results of polyacrylamide gel electrophoresis.

The PSC compositions disclosed herein comprise a yeast aerobic fermentation supernatant, surface-active agents and stabilizing agents. *Saccharomyces cerevisiae* is grown under aerobic conditions familiar to those skilled in the art, using a sugar source, such as molasses, or soybean, or corn, or cane sugar, as the primary nutrient source. Alternative types of yeast that can be utilized in the fermentation process may include: *Kluyeromyces maxianus, Kluyeromyces lactus, Candida utilis* (Torula yeast), *Zygosaccharomyces, Pichia* and *Hansanula*. Those skilled in the art will recognize that other and further yeast strains are potentially useful in the fermentation and production of the low molecular weight proteins, "the protein system." It should be understood that these yeasts and the yeast classes described above are identified only as preferred materials and that this list is neither exclusive nor limiting of the compositions and methods described herein.

The proteins of the disclosed PSC compositions comprise proteins, protein fragments, peptides, and stress proteins having a size less than 30 kDa. In some embodiments, the size range is from about 0.5 kDa to about 30 kDa. Throughout the present disclosure, the protein mixture used in the PSC compositions disclosed herein is referred to as the "protein system."

The word "peptide" includes long chain polypeptides, such as proteins, as well as short chain peptides, such as dimers, trimers, oligomers, and protein fragments. In some embodiments, the words "polypeptide" and "protein" are interchangeable.

In some embodiments, the protein mixture of the PSC compositions disclosed herein are derived from a fermentation of *Saccharomyces cerevisiae*, which, when blended with surface active agents or surfactants, enhance multiple chemical functions. The protein systems disclosed herein can also be derived from the fermentation of other yeast species, for example, *kluyveromyces marxianus, kluyveromyces lactis, candida utilis, zygosaccharomyces, pichia,* or *hansanula*. In a preferred embodiment, the fermentation process is aerobic.

After the aerobic fermentation process, a fermentation mixture is obtained, which comprises the fermented yeast cells and the proteins and peptides secreted therefrom. In some embodiments, the fermentation mixture can be subjected to additional stress, such as overheating, starvation, overfeeding, oxidative stress, or mechanical or chemical stress, to obtain a post-fermentation mixture. The additional stress causes additional proteins ("stress proteins") to be expressed by the yeast cells and released into the fermentation mixture. These additional proteins are not normally present in significant quantity during a simple fermentation process. Once the post-fermentation mixture is centrifuged, the resulting supernatant comprises both the stress proteins and proteins normally obtained during fermentation. The post-fermentation mixture may then be stabilized to prevent degradation or bacterial contamination through the use of antimicrobial agents, preservatives and/or pH adjustment. The compositions described herein comprise stress proteins.

Some embodiments of fermentation processes used for the current invention are described in the above-incorporated patents. In addition, in some embodiments the ratio of fermentation supernatant to surfactant(s) may vary in a broad range, but in instances where emulsifying effect is undesirable, it has been found that interfacial tension of the aqueous solution can be reduced with higher protein (supernatant) ratio relative to the amount of surfactant. The broad range of functionality gives the formulator flexibility in optimizing products for specific end uses. In some embodiments, the ratio of fermentation supernatant to surfactant is in the range of 1 to 3. Alternatively, the protein ratio might be much less than 1.

An embodiment of the methods disclosed herein is now described with reference to FIG. 1. A container 102 contained water or brine. In some embodiments, the salinity of the water in the container is adjusted to simulate sea water. An oil spot 104 was created in the middle of the container. Because of the immiscibility of water and oil and their relative densities, the oil spot generally remained at the surface of the water. An oil-absorbing pad 106 was placed at the perimeter of the water surface. A surfactant solution containing the PSC compositions disclosed herein was added to the oil spot 104 using a dropper 108. Immediately after injecting the surfactant solution, a clear, oil-free spot appears at the site of injection and spreads outwardly in the direction of arrows 112, causing water circulation within the container 102 in the direction of arrows 110. This movement of water causes the oil to move in the direction of arrows 112 towards the oil-absorbing pad 106 at the perimeter. At the conclusion of the experiment, oil is completely taken by the encircling pad 106. The oil-soaked pad 114 was then removed from the container 102. In some embodiments, The oil-soaked absorbing pad 114 is either recycled by squeezing out the oil into a collector container, while the pad can be used again, or, if it is economically sound, to use the oil-loaded pad 114 as a fuel, to combust it, e.g. in a power station, in combination with another fuel such as coal.

In one example, the container 102 was a 2-liter container with brine (3.5% sodium chloride) and the oil spot 104 was created by layering 10 g of Texas crude to form a spot of approximately 6 cm in diameter. The surfactant successfully applied to achieve prompt and uniform oil motion away from the surfactant injection point, while forming a clear spot in the middle, was a blend of the yeast fermentation derived yeast proteins mixed with anionic and nonionic surfactants.

In some embodiments, the surfactant has a relatively low affinity to oil, so as to concentrate at the aqueous surface, but not disperse the oil due to the formation of a microemulsion, rather than moving oil away from the point of injection. Rather high HLB value of surfactant is important to prevent the interference of surfactant with the process of oil uptake by the oil-absorbing boom The oil-absorbing pad 106 in the above example was cut out of a Heavy Fine Polypropylene Fiber Bonded Oil-Only Pads supplied by the CP Lab Safety Corp., although any other brand of essentially hydrophobic material with a highly developed internal surface is acceptable, provided it can be confined in a certain geometrical entity. One advantage of the material used in the example is that it is highly hydrophobic, i.e. water rejecting, but actively attracts and absorbs hydrocarbons.

When the front of the spreading clean water in the middle of the oil spot pushes the oil to the extent that it comes into a contact with the pad, oil is absorbed completely, and no water is absorbed by the pad.

The aforementioned procedure is highly scalable, and has been successfully tested in removal of oil spots from the surface of a pond and the ocean.

In another aspect, disclosed herein is the calculative procedure for the estimation of the amount of surfactant needed to clear an oil spot, based on the dimensions of the encircled area. The calculation is based on the assumption (generally accepted in surface science), that at least a monomolecular film must be formed on the surface to decrease the surface tension and thus induce the inflow of water from the bulk to the surface. According to the literature [see, e.g. Colloids and Surfaces A: Physicochemical and Engineering Aspects 164 (2000) 9-18], the molecular area of common surfactants varies within the limits of 10 to 100 Å$^2$, with the trend of being reduced in the mixtures of surfactants of different types (such as ionic and non-ionic).

For the sake of reliability, the lower limit of 10 Å$^2$ is used in the following calculations. The molar mass of common surfactants is within the range of 200 to 600 g/mol. For the estimation purposes, the mean value at 400 g/mol is used. Under these assumptions, $$\frac{10 \text{Å}^2}{\text{molecule}} \times \frac{10^{-20} \text{m}^2}{\text{Å}^2} \times \frac{6 \times 10^{23} \text{ molecules}}{\text{mol}} = 6000 \text{ m}^2/\text{mol}$$

The area per unit weight and per unit volume is than calculated as follows:

$$6000 \text{ m}^2/\text{mol} \div 400 \text{ g/mol} = 15 \text{ m}^2/\text{g}$$

$$15 \text{ m}^2/\text{g} \times 1000 \text{ g/kg} \times 1 \text{ kg/L} = 15{,}000 \text{ m}^2/\text{L}$$

Conversely, the dose rate per square meter is about 0.07 g/m², or 70 g per 1000 m², or about 7 g per 1000 sq. ft.

Surfactants are commonly applied as an aqueous solution of a certain percent concentration by weight, n %, in active ingredients. Then the dose rate is determined as (7/n) g/m², or (7/n) kg per 1000 m², or (0.7/n) kg per 1000 sq ft, and, with a very rough, but reasonable rounding off, (1/n) L per 1000 sq ft, or (0.2/n) gallon/per 1000 sq ft.

The amount of absorbing material in the encircling boom may be estimated out of the absorption capacity of the absorbing material. The latter is determined for some materials currently on the market as up to 20 times the weight of the absorbed oil to the weight of the absorbent itself. For instance, the materials marketed by ChemTex Inc., Cumberland, R.I., absorb 68 gal of oil per 30 lb of absorbent pad [http://www.chemtexinc.com/oilonly.html]. PCI Products Co, Chino Hills, Calif. markets a 5 inches×40 ft oil-only absorbing boom with a weight of 22 lbs, which absorbs 30 gallons of oil.

Therefore, given the above numbers, for a spill of A surface area, with a certain average depth h, the amount of oil in the spill may be estimated as (8A×h) kg, if A is in square meters and the depth h is in centimeters; and oil density is about 0.8 kg/L. The depth of the spot depends on the characteristics of oil. It can be either measured on site, or estimated out of the characteristics of oil: for the initial time after the spill of a rather thin Light Crude oil occurred, and has not yet been weathered, the depth may be expected to be at 1 cm level.

Hence, the amount of absorbing material in the encircling booms may be estimated as 1/20 of the above, but for reliability, a certain excess is desirable, leading to about (0.5A×h) kg of oil-only absorbing boom, where A is the area of the spill in square meters and h is the depth of the spill in centimeters.

What is claimed is:

1. A method of removing oil from an aqueous surface, the method comprising:
   surrounding an oil spot on the aqueous surface with an oil-absorbing material; and
   introducing a solution comprising a protein/surfactant complex to the oil spot, wherein the protein/surfactant complex comprises a protein component obtained from the fermentation of yeast, wherein the protein component comprises a mixture of multiple intracellular proteins, at least a portion of the mixture including yeast polypeptides obtained from fermenting yeast and yeast stress proteins resulting from subjecting a mixture obtained from the yeast fermentation to stress.

2. The method of claim 1, wherein, after the surrounding step, the method does not include the step of mechanically directing the oil towards the oil-absorbing material, or the step of mechanically directing the oil-absorbing material towards the oil.

3. The method of claim 1, wherein the oil-absorbing material is made from a material selected from the group consisting of sponge, hair, hay, and absorbent polymers.

4. The method of claim 1, wherein the oil-absorbing material is contained in a water and oil permeable casing.

5. The method of claim 4, wherein the casing is configured to allow contaminated water and oil to come into contact with the oil-absorbing material, but not to allow the oil-absorbing material to escape the casing.

6. The method of claim 1, wherein the protein component is from aerobic fermentation of yeast.

7. The method of claim 1, wherein the protein component comprises proteins obtained from exposing a product obtained from the fermentation of yeast to additional procedures that increase the yield of proteins produced from the process.

8. The method of claim 1, wherein the protein component comprises proteins obtained from exposing a product obtained from the fermentation of yeast to an additional procedure selected from the group consisting of heat shock of the fermentation product, physical and/or chemical disruption of the yeast cells to release additional polypeptides, and lysing of the yeast cells.

9. The method of claim 1, wherein the protein component comprises proteins obtained from exposing a product obtained from the fermentation of yeast to heat shock conditions.

10. The method of claim 1, wherein the protein component comprises proteins obtained from physically disrupting the yeast after the fermentation of the yeast.

11. The method of claim 1, wherein the protein component comprises proteins obtained from chemically disrupting the yeast after the fermentation of the yeast.

12. The method of claim 1, wherein the protein component comprises proteins obtained from lysing the yeast after the fermentation of the yeast.

13. The method of claim 1, wherein the surfactant has strong affinity to water, and weak affinity to oil, thereby preventing an oil dispersion effect.

14. The method of claim 1, wherein the surfactant is selected from the group consisting of nonionic surfactants, anionic surfactants, amphoteric surfactants, cationic surfactants, and a combination thereof.

15. The method of claim 1, wherein the surfactant is non-petroleum based.

16. The method of claim 1, wherein the solution comprising the surfactant is injected into the center of the oil spot.

17. A method of removing oil from an aqueous surface, the method comprising:
   surrounding an oil spot on the aqueous surface with an oil-absorbing material; and
   introducing a solution comprising a protein/surfactant complex to the oil spot, wherein the protein/surfactant complex comprises a protein component obtained from the fermentation of yeast, wherein the protein component comprises a mixture of multiple intracellular proteins, at least a portion of the mixture including yeast polypeptides obtained from fermenting yeast and yeast stress proteins resulting from subjecting a mixture obtained from the yeast fermentation to stress,
   wherein the oil is not mechanically directed towards the oil-absorbing material, or
   wherein the oil-absorbing material is not mechanically directed towards the oil.

* * * * *